United States Patent [19]

Donahue

[11] Patent Number: 5,282,821
[45] Date of Patent: Feb. 1, 1994

[54] ADJUSTABLE SURGICAL INSTRUMENT

[76] Inventor: John R. Donahue, 530 Rosedale Dr., Pottstown, Pa. 19464

[21] Appl. No.: 8,913

[22] Filed: Jan. 26, 1993

[51] Int. Cl.$^5$ ............................................... A61B 17/32
[52] U.S. Cl. .................................... 606/170; 606/180; 604/22
[58] Field of Search ............... 606/167, 170, 171, 180; 128/4, 6, 750–757; 604/22

[56] References Cited

U.S. PATENT DOCUMENTS

| | | |
|---|---|---|
| 1,636,636 | 7/1927 | Humble .............................. 606/180 |
| 3,890,977 | 6/1975 | Wilson . |
| 4,203,444 | 5/1980 | Bonnell et al. . |
| 4,274,414 | 6/1981 | Johnson et al. . |
| 4,646,738 | 3/1987 | Trott . |
| 4,665,906 | 5/1987 | Jervis . |
| 4,705,038 | 11/1987 | Sjostrom et al. . |
| 4,834,729 | 5/1989 | Sjostrom . |
| 4,842,578 | 6/1989 | Johnson et al. . |
| 4,983,179 | 1/1991 | Sjostrom . |
| 5,067,957 | 11/1991 | Jervis . |
| 5,152,744 | 10/1992 | Krause et al. . |

Primary Examiner—Stephen C. Pellegrino
Assistant Examiner—William Lewis
Attorney, Agent, or Firm—Michael F. Petock

[57] ABSTRACT

An adjustable surgical instrument is provided in which adjustment of curvature may be provided during the surgical procedure while the instrument is within a body cavity. The adjustment of curvature may be made from no curvature, that is, straight, to ninety degrees or more. A surgical instrument is provided with an outer, intermediate and inner hollow member. The hollow intermediate member is mounted within the outer hollow member, and is provided with a preformed curvature, preferably in its distal region. The intermediate member is provided with a preformed curvature, preferably in its distal region, which curvature may be reduced or eliminated by longitudinally moving the outer hollow member over the curvature in the hollow intermediate member. The intermediate member has memory such that the initial curvature is recovered upon removal of the hollow outer member from the area of curvature of the intermediate hollow member. An inner member having flexibility at least in the area of curvature is provided with a cutting implement on its distal end. A drive is provided for displacing the hollow outer member with respect to the hollow intermediate member in a longitudinal direction.

10 Claims, 2 Drawing Sheets

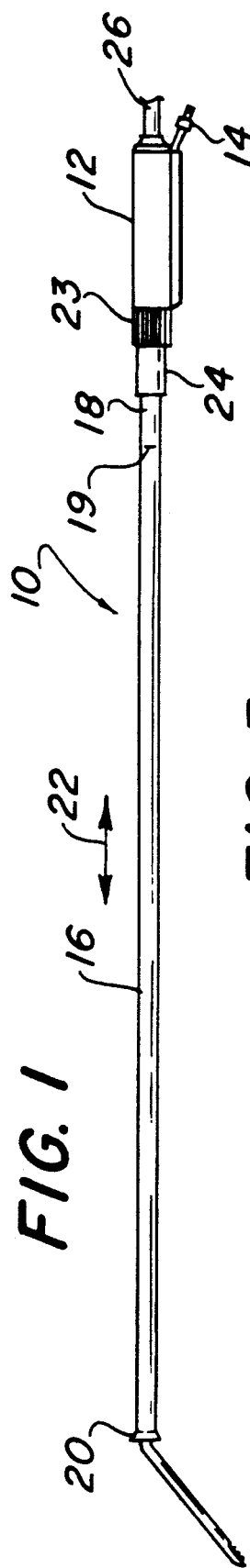
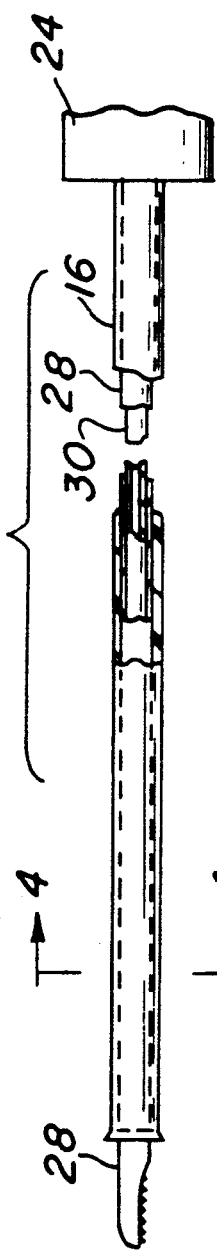
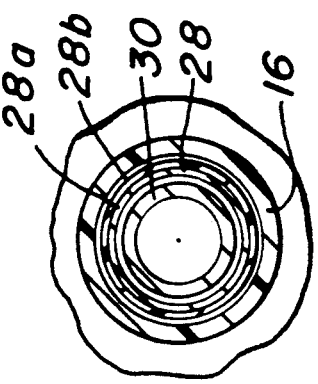
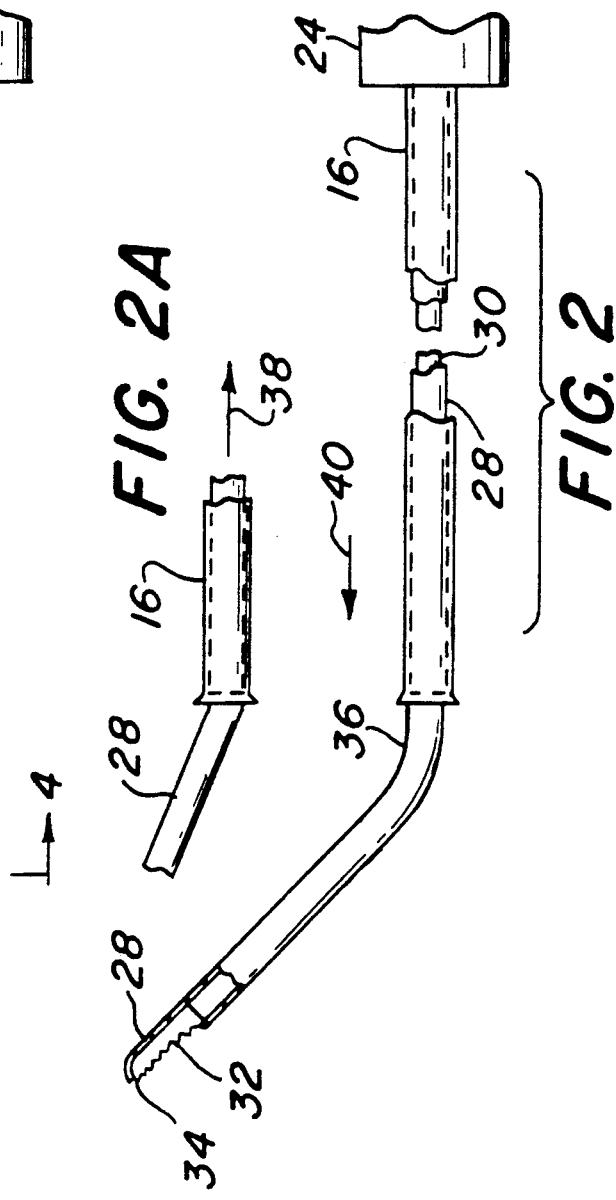

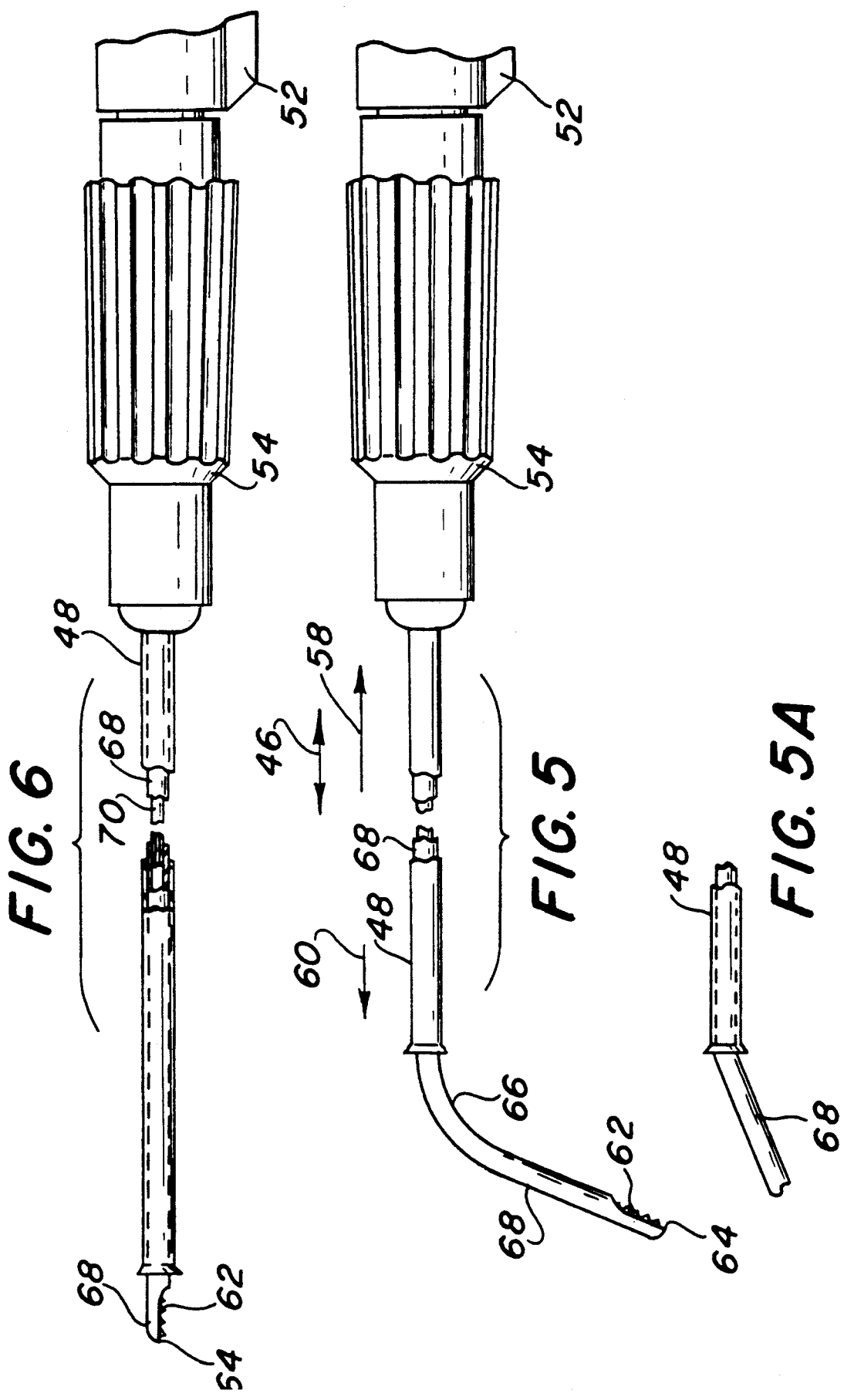

ADJUSTABLE SURGICAL INSTRUMENT

BACKGROUND OF THE INVENTION

This invention relates to a surgical instrument, and in particular to adjustable arthroscopic surgical instruments.

Arthroscopic surgical instruments typically include a rigid outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument. Examples of such surgical instruments are described in U.S. Pat. No. 4,203,444—Bonnell et al.; U.S. Pat. No. 4,274,414—Johnson et al.; and U.S. Pat. No. 4,842,578—Johnson et al.

The aforesaid typical arthroscopic surgical instruments are linear, or in other words, straight between their proximal and distal ends. Such linear or straight instruments have limitations and disadvantages in many surgical operations, as most body parts and cavities of humans and animals are not straight, but have curved and/or irregular surfaces. It has been recognized that it is sometimes useful for such instruments to be curved to facilitate positioning the cutting implement against the tissue, bone or cartilage to be cut.

Accordingly, more recently, arthroscopic surgical instruments have been developed which have a fixed bend or curve placed in the rigid outer tube at the time of fabrication of the instrument. Examples of such instruments with such fixed bends or curves in the rigid outer tube are described in U.S. Pat. No. 4,646,738—Trott and U.S. Pat. No. 5,152,744—Krause et al. Both of these patents disclose a rigid outer tube with a predetermined bend therein which is placed and fixed in the instrument at the time of fabrication of the instrument. At least a portion of the inner tube for transmitting torque to the cutting blade is made flexible such that it freely rotates within the bend in the outer rigid tube.

SUMMARY OF THE INVENTION

The present invention provides a surgical instrument which may be introduced into a body cavity through a small incision, and may be provided with a degree of curvature during the surgical procedure while the instrument is in the body. This instrument provides the surgeon with a great degree of flexibility during the surgical procedure, wherein the curvature of the instrument may be adjusted while the instrument is in the body to suit the desired needs of the surgeon. The instrument may be viewed during the surgical procedure by a scope inserted through another incision. The scope may be of any suitable type, including those directly viewable through a lens or a video scope which is connected to a monitor.

The present invention provides a surgeon with a great degree of flexibility, wherein a surgical procedure may be performed more easily and more accurately with less discomfort to the patient. This enables the surgeon to more quickly and effectively perform the surgery, and enables more surgical procedures to be performed more effectively under local anesthesia. The instrument provides greater flexibility in any of the surgical procedures now commonly performed through a small incision, such as laparoscopic surgery, gynecological surgery performed through the vagina, colonoscopic surgery and particularly, arthroscopic surgery, where it is often necessary for the instrument to be accurately placed into the curved spaces between the bones of the joint.

In accordance with the method and apparatus of the present invention, greater flexibility is provided to the surgeon by enabling the surgeon to insert the instrument of the present invention into the body cavity, such as a joint, visualize by means of a scope (which may be a direct lens or a video scope connected to a video display) the nature and location of a desired bend or curve to be placed in the instrument, and adjust the curvature of the instrument while the instrument is in the body cavity.

Accordingly, in accordance with the present invention, the surgical instrument is constructed for insertion into a body for cutting wherein it includes a hollow outer member, intermediate member and inner member in which the curvature of the intermediate member (and accordingly the curvature of the inner member) may be adjusted. The hollow outer member has an open distal end and an open proximal end with the hollow intermediate member mounted within it. The intermediate member is provided with at least one opening in a distal region thereof. The hollow intermediate member is provided with a preformed curvature in a portion of its length distally. The intermediate member is deformable so as to reduce the amount of curvature upon the application of a predetermined force, and is provided with a memory such that the initial curvature is recovered upon removal of the force. The hollow inner member is disposed within the intermediate member for transmitting force applied to a proximal end to move a cutting implement disposed at a distal end. The cutting implement is constructed and adapted to perform a cutting function at the opening in the intermediate member. The inner member is flexible at least in the area of curvature of the intermediate member, and a drive is provided for displacing the hollow outer member with respect to the hollow intermediate member along their longitudinal axes, wherein the amount of curvature of the intermediate member may be controlled.

In accordance with the present invention, the method includes the steps of inserting such an instrument into a body cavity and visualizing the instrument in the cavity with respect to the natural curvatures of the body components. The method further includes the step of adjusting the longitudinal position of the outer hollow member in relation to the intermediate hollow member to adjust the amount of curvature in the intermediate hollow member during the performance of the surgical procedure.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 1 is an elevation view of an adjustable surgical instrument in accordance with the present invention.

FIG. 2 is an elevation view of a portion of an adjustable surgical instrument in accordance with the present invention shown in a curved condition and partially broken away to reveal components.

FIG. 2A is a broken away portion of the instrument of FIG. 2 illustrating the outer hollow member in an intermediate position resulting in a lesser amount or degree of curvature.

FIG. 3 is an elevation view of an adjustable surgical instrument shown in a straight condition and partially broken away to show components.

FIG. 4 is a cross-sectional view taken along line 4—4 of FIG. 3.

FIG. 5 is a plan view of another embodiment of an adjustable surgical instrument in accordance with the present invention shown in a curved condition and partially broken away to show components.

FIG. 5A is a broken away portion of the instrument of FIG. 5 illustrating the outer hollow member in an intermediate position resulting in a lesser amount or degree of curvature.

FIG. 6 is an elevation view of the same instrument shown in FIG. 5 in the straight condition and partially broken away to show components.

DETAILED DESCRIPTION OF THE PREFERRED EMBODIMENTS

Referring now to the drawings in detail, wherein like numerals indicate like elements, there is shown in FIG. 1 an adjustable surgical instrument 10. Adjustable surgical instrument 10 is provided with a handpiece 12 which contains a motor and a suction connection 14 to which a partial vacuum is applied. Adjustable surgical instrument 10 has an outer hollow member 16 with a proximal end at 18 and a distal end at 20. Outer hollow member 16 is a rigid tube, and is movable in the directions of double-headed arrow 22 by means of a drive 24. Drive 24 may be powered by the motor contained in hand-held unit 12 utilized to drive the cutter at the distal end, or may be provided with its own separate motor. Drive 24 may be controlled by switches mounted on hand-held unit 12, by foot controls which are connected by means of wires contained in cable 26 or by other suitable means.

Within the outer rigid hollow member 16, there is contained an intermediate hollow member 28. Within intermediate hollow member 28, there is contained an inner hollow member 30, which is provided with a cutting implement 32 in its distal region. The structure of the intermediate and inner hollow members may be best seen in FIGS. 2, 3 and 4, and will be described in greater detail hereinafter. Intermediate hollow member 28 is provided with an opening 34 in its distal region through which cutter 32 is exposed to tissue to be cut. The teachings of my copending application entitled "FLEXIBLE SURGICAL INSTRUMENT", U.S. application Ser. No. 08/008,918, filed Jan. 26, 1993, the same day as this application, are incorporated herein by reference the same as if set forth at length. The structure of the adjustable surgical instrument illustrated in FIGS. 1 through 4 is identical, except for the fact that FIG. 1 illustrates the opening 34 in intermediate hollow member 28 as being on the inside of the curvature of intermediate hollow member 28 in FIG. 1, and being on the outside of the curvature in FIG. 2. This opening may be placed as desired, but it is preferably placed on the inside of the curvature as shown in FIGS. 1 and 5. Except for this difference, all of the other structure is the same, and the same reference numerals will be utilized to describe and illustrate the operative structure.

Intermediate hollow member 28 is provided with a preformed curvature in a distal region at 36. The preformed curvature may be located at various positions along the length of member 28, so long as this curvature is located distally of the distal end of member 16 when member 16 is moved to its most proximal position by drive 24. Intermediate member 28 is deformable so as to reduce the amount of curvature, that is, tending to straighten it or to completely straighten it, upon the application of a force in a direction opposite to the direction of curvature. Intermediate hollow member 28 has a memory or resiliency such that the initial curvature is recovered upon the removal of the force. Materials of this type are currently known, and are commercially available. Attention is directed to U.S. Pat. Nos. 5,067,957 and 4,665,906, which disclose some examples of such materials. Any suitable material which may be provided with a resiliency or memory such that it may be provided with a preset curve, controllably straightened and provided with the ability to recover or remember its initial curve upon removal of the straightening force, may be utilized in the practicing of the present invention.

Referring now particularly to FIGS. 2 and 3, there is shown in FIG. 2 the outer substantially rigid hollow member 16 which may be moved in the direction of its longitudinal axis, that is in the directions of double-headed arrow 22, by means of a drive contained in 24. As shown in FIG. 2, hollow outer member 16 has been moved proximally in the direction of arrow 38, thereby allowing intermediate hollow member 28 to display or recover its preformed curvature at 36. By moving outer hollow member 16 distally in the direction of arrow 40, a selective, controllable straightening or reduction in the amount of curvature of intermediate hollow member 28 is achieved, as shown in FIG. 2A. In this manner, the amount of curvature may be controllably selected from zero curvature to the maximum preformed or preset curvature in intermediate hollow member 28. The curvature in intermediate hollow member 28 may be any selected preset amount, and typically approaches ninety degrees, although the amount of curvature can be preformed to be substantially less or substantially greater, and even greater than ninety degrees.

As described above, an inner hollow member 30 is mounted within intermediate hollow member 28, and is provided with a cutting implement 32 mounted to its distal end. The cutting implement may be any suitable type of cutting implement, such as those typically utilized in arthroscopic blades, including cutters and burrs, with the cutting blade attached to the distal end of inner hollow member 30. This may be attached adhesively or otherwise bonded as described in my copending application referred to above. Inner hollow member 30 may be flexible for the entire length of intermediate hollow member 28, or it may be provided with a flexible portion in the area of the preformed curvature. In any event, inner hollow member 30 is provided with flexibility at least in the area of the preformed curvature in intermediate member 28. Inner member 30 functions to transmit force applied to its proximal end to move cutting implement 32 disposed at its distal end. Typically, hollow member 30 transmits the force by rotation to cause rotation of a cutting implement 32, although it is understood that other forms of motion may be transmitted, including a longitudinal reciprocating motion. Preferably, and as illustrated in the drawings, inner member 30 is hollow such that irrigating fluids and tissue cut by the cutting implement 32 may be removed by suction through tube 30, and suction connection 14. As used herein, the term "tissue" is understood to mean broadly all components of the body made up of cells and intercellular material, including not only soft tissue, but also cartilage, bone and the like.

All of the tubular materials and other components described herein may be made of suitable metals or plastics or combinations of the same so long as they provide a sufficient degree of rigidity or flexibility for the operations as described above and hereinafter with respect to FIGS. 5, 5A and 6. The intermediate hollow deformable member, identified as 28 above and 68 infra, may be comprised of an inner layer 28a of metal, such as a titanium alloy having the required resiliency and memory, and an outer layer 28b of a suitable friction-reducing plastic. This enables reduced friction where the end of the outer sleeve is forced over the area of preformed curvature in the intermediate member. However, it is understood that other variations and combinations of material fall within the scope and spirit of the present invention where the essential functions as described herein may be achieved.

As illustrated in FIG. 1 at 19, the outer hollow member 16 may be detachable or removable from the gear drive 24. This may be accomplished within gear drive 24, or, as illustrated by the break line 19, by a threadable insertion or other connection or union between components which make up the outer hollow member 16. The portion of outer hollow member 16 between point 19 and its distal end 20 may serve as a cannula (that is, in place of the cannula normally used) for the surgical instrument incision. This effectively allows use of a smaller diameter of cannula, as compared to the size of cannula that would be required if outer hollow tube 16 were required to pass through it. The use of a detachable outer hollow member 16 or a detachable portion of outer hollow member 16 allows for the selection of different lengths of outer hollow member to be selected, thereby providing added flexibility in the surgical instrument.

The surgical instrument 10 may be optionally provided with a rotator element 23 which may be utilized to manually or by use of a motorized drive selectively rotate intermediate member 28 to selectively position the azimuth of the curvature in the intermediate member. In other words, by rotating unit 23, with the outer hollow member 16 in a proximally retracted position, the direction of the curved distal end of intermediate member 28 may be made to point in any angular degree from zero to 360 degrees. If rotator element 23 is motorized, it may be driven by a second drive from the same motor in unit 12 with appropriate gear reduction and controlled by a switch on unit 12 and/or a foot pedal.

Referring now to FIGS. 5 and 6, there is shown another embodiment of the present invention, wherein outer hollow member 48 may be moved along its longitudinal axis, that is, in the directions of double-headed arrow 46 by means of a manually operable drive 54. The instrument of FIGS. 5 and 6 is substantially identical to that as described with respect to FIGS. 1 through 4, except that the drive for longitudinally moving outer hollow member 48 in the direction of double-headed arrow 46 is done manually by turning or rotating a rotation knob 54 which threadably causes outer hollow member 48 to be proximally retracted in the direction of arrow 58, or moved distally in the direction of arrow 60. When substantially rigid outer hollow member 48 is moved in the direction of arrow 60, there is controlled straightening or reduction in the amount of curvature of intermediate hollow member 68. This causes a reduction in the amount of curvature at 66 as illustrated in FIG. 5A. Continued movement of outer hollow member 48 in the direction of arrow 60 results in substantial straightening of intermediate hollow member 68 as illustrated in FIG. 6, that is, zero curvature.

As described with respect to FIGS. 1 through 4, intermediate hollow member 68 is provided with an opening 64 in its distal region through which a cutting implement 62 is exposed to enable the cutting of tissue. The opening 64 in intermediate member 68 is provided on the inside of the curve, or in other words, in the direction which member 68 moves when outer hollow member 48 is retracted proximally. This is the presently preferred location in that it is believed that it would be useful in most surgical cases, but it is understood that opening 64 may be placed anywhere in the distal regions of intermediate members 68 and 28, including the opposite surface, or on the lateral surfaces thereof. As described previously, the cutting implement 62 is caused to be moved or operated by the inner hollow member 70, which is preferably a rotary movement, but may be a longitudinal movement. As described previously, irrigating fluid and cut tissue are removed through hollow member 70 by means of a suction or partial vacuum. The force, usually a rotary force, applied to member 70 is provided by a motor contained in handpiece 52.

It is understood that various other means may be utilized to provide the manual force to drive outer hollow member 48 longitudinally in the directions of double-headed arrow 46. For example, instead of a ridged rotation member 54 as shown, a short lever may project radially which may be rotated by the thumb and fingers to cause a threadable adjustment in the longitudinal direction utilizing a worm gear drive. Alternatively, a slide mechanism, such as a slide lever, may be utilized to slide outer rigid hollow member 48 in the directions of double-headed arrow 46. This may utilize a frictional engagement or a detent mechanism. It will be apparent to those skilled in the art that numerous other similar variations may be made to the manner of practicing the present invention within the scope and spirit of the present invention.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A surgical instrument that is constructed for insertion into a body for cutting, comprising:
    a hollow outer member having an open distal end and an open proximal end;
    a hollow intermediate member mounted within said outer hollow member, said intermediate member having at least one opening in a distal region thereof;
    said hollow intermediate member having a preformed curvature in a portion of its length, said intermediate member being deformable so as to reduce the amount of curvature upon the application of a predetermined force and having memory such that said initial curvature is recovered upon removal of said force;

a hollow inner member disposed within said intermediate member for transmitting force applied to a proximal end to move a cutting implement disposed at a distal end, said cutting implement being constructed and adapted to perform a cutting function at said opening in said intermediate member;

said inner member being flexible at least in the area of said curvature in said intermediate member; and a drive for displacing said hollow outer member with respect to said hollow intermediate member along their longitudinal axes wherein the amount of said curvature of said intermediate member may be controlled.

2. A surgical instrument in accordance with claim 1 wherein said drive is manually operable.

3. A surgical instrument in accordance with claim 1 wherein said drive is motorized.

4. A surgical instrument in accordance with claim 1 wherein said preformed curvature is in a distal region of said intermediate hollow member.

5. A surgical instrument in accordance with claim 1 including a second drive for rotating said hollow intermediate member to a selected rotational position.

6. A surgical instrument in accordance with claim 5 wherein said second drive is a manual drive.

7. A surgical instrument in accordance with claim 5 wherein said second drive is a motorized drive.

8. A method of performing a surgical procedure involving cutting in a body, comprising the steps of:

inserting a surgical instrument having a hollow outer member, a hollow intermediate member mounted within said outer hollow member, said intermediate member having at least one opening in a distal region thereof and a preformed curvature, said intermediate member being deformable so as to reduce the amount of curvature upon the application of a predetermined force, and having memory such that said initial curvature is recovered upon removal of said force, and a hollow inner member disposed within said intermediate member for transmitting force applied to a proximal end to move a cutting implement disposed at the distal end to perform a cutting function at said opening in said intermediate member;

visualizing said instrument via a scope inserted through a second incision to view the relationship between the surgical instrument and the natural curvatures of the body components; and adjusting the longitudinal position of the outer hollow member in relation to the intermediate hollow member to adjust the amount of curvature in the intermediate hollow member.

9. A method in accordance with claim 8 wherein the step of adjusting the longitudinal position of the outer hollow member in relation to the intermediate hollow member is performed manually.

10. A method in accordance with claim 8 wherein the step of adjusting the longitudinal position of the outer hollow member in relation to the intermediate hollow member is performed utilizing a motorized drive.

* * * * *